US005682876A

United States Patent [19]
Pernetti et al.

[11] Patent Number: 5,682,876
[45] Date of Patent: Nov. 4, 1997

[54] ABSORBER SWITCH LOCKING DEVICE

[75] Inventors: Denise L. Pernetti, Cottage Grove; Richard C. Fries, Madison, both of Wis.

[73] Assignee: Ohmeda Inc., Liberty Corner, N.J.

[21] Appl. No.: 620,052

[22] Filed: Mar. 20, 1996

[51] Int. Cl.⁶ .................................................. A61M 16/00
[52] U.S. Cl. .................. 128/202.27; 128/203.28; 128/205.13; 128/205.17
[58] Field of Search .................. 128/203.28, 205.13, 128/205.14, 205.15, 205.17, 205.24, 202.27

[56] References Cited

U.S. PATENT DOCUMENTS

| 4,181,512 | 1/1980 | Kippel et al. | 128/205.29 |
| 4,596,246 | 6/1986 | Lyall | 128/202.27 |
| 4,991,576 | 2/1991 | Henkin et al. | 128/203.28 |
| 5,284,160 | 2/1994 | Dryden | 128/203.12 |

FOREIGN PATENT DOCUMENTS 2243733  3/1974  Germany ........................ 128/202.27

Primary Examiner—V. Millin
Assistant Examiner—William J. Deane, Jr.
Attorney, Agent, or Firm—Roger M. Rathbun; Salvatore P. Pace

[57] ABSTRACT

A locking device is disclosed for attachment to an absorber used in an anesthesia system and which provides assurance that the bag to ventilator switch cannot be put in the ventilator position for those applications where a ventilator is not intended to be used, i.e. MRI applications. As a further feature, the locking device also physically prevents the ventilator input to the bag to ventilator switch from being occluded, either by a protective plastic shipping cap or by having tubing or other conduits connected thereto.

11 Claims, 4 Drawing Sheets

ABSORBER SWITCH LOCKING DEVICE

BACKGROUND OF THE INVENTION

The present invention relates to an absorber used in a medical anesthesia system and, more particularly, to a safety locking device for attachment to the absorber head to prevent an undesirable condition.

Generally, in anesthesia systems used to provide a vaporized anesthetic to a patient to anesthetize the patient while undergoing surgery, an absorber is used to remove $CO_2$ that is circulating in the system from the patient's exhalation. Since the system provides certain rebreathing of the patient's exhalation, the build up of an excessive amount of $CO_2$ is obviously an undesirable effect.

Accordingly, the absorber is introduced into the flow of gas within the patient anesthesia system circuit and contains an absorbent to remove $CO_2$ that circulates within the anesthesia system.

In the typical absorber, the unit also contains other functions within the head of the unit, such functions including various ports for the receipt and delivery of gasses as well as a switch that allows the anesthesiologist to select either the use of a mechanical ventilator that supplies the breath to the patient or, alternatively, the use of a flexible bag that is manually squeezed by the anesthesiologist to provide that breath to the patient.

That switch is commonly referred to as the bag to ventilator switch and by rotating the switch, the anesthesiologist can make the desired selection between manual bagging the patient or utilizing the ventilator to carry out the respiration of the patient.

In certain operations, the ventilator choice is not utilized, a typical use being where the patient is undergoing a MRI or magnetic resonance imaging procedure. With MRI use, the anesthesiologist uses the bag mode exclusively and the ventilator mode, although present, is not an option.

In certain instances, it is possible to achieve an undesirable condition where the anesthesiologist desires to utilize the bag but inadvertently has left the bag to ventilator switch in the ventilator position. That situation is aggravated where the normal inlet port from the ventilator is also sealed such as with the normal plastic sealing cap provided on the absorber by the manufacturer for shipment to keep the internal passages clean prior to actual use.

With those conditions present, there is no effective pressure relief within the anesthesia system and the pressure in that system is continually raised by the continued inflow of fresh gas into the system. Undesirable levels of pressure can thus be attained in the patient circuit and affect the lungs of the patient.

In addition, if that bag to ventilator switch is in the ventilator position and the normal plastic cap is not present, the overall system can continually lose pressure through that input.

SUMMARY OF THE INVENTION

The absorber switch locking device of the present invention provides a relatively simple solution to the problem of an excessive pressure being produced in the patient breathing circuit through the specific conditions where the bag to ventilator switch is inadvertently in the ventilator position and also there is still the protective cap on the ventilator inlet to that switch that occludes the flow through that ventilator inlet. Also, when the bag to ventilator switch is in the ventilator position and the protective cap is not in place, the consequent loss of pressure problem is prevented.

In accordance with this invention, a locking device has been developed that is affixed to the frame of the absorber and which prevents the bag to ventilator switch from being turned to the ventilator position. In addition, the same locking means has a further feature that prevents the ventilator inlet to that switch from being closed or plugged. In that way, the user is assured that the protective cap is not occluding the ventilator inlet opening and that no additional tubing or the like has been connected to that inlet that also may be occluded.

Accordingly, the present invention can be factory installed on those anesthesia systems designed and sold specifically for use in MRI applications and where the ventilator mode is not intended to be used. In addition, the present invention can be readily retrofitted to current absorbers that are in the field to provide the protection to those units.

Other objects, features and advantages of the present invention will be more apparent from the detailed description of the preferred embodiments set forth below, taken in conjunction with the accompanying drawings.

DESCRIPTION OF THE PREFERRED EMBODIMENT

Figure 1:
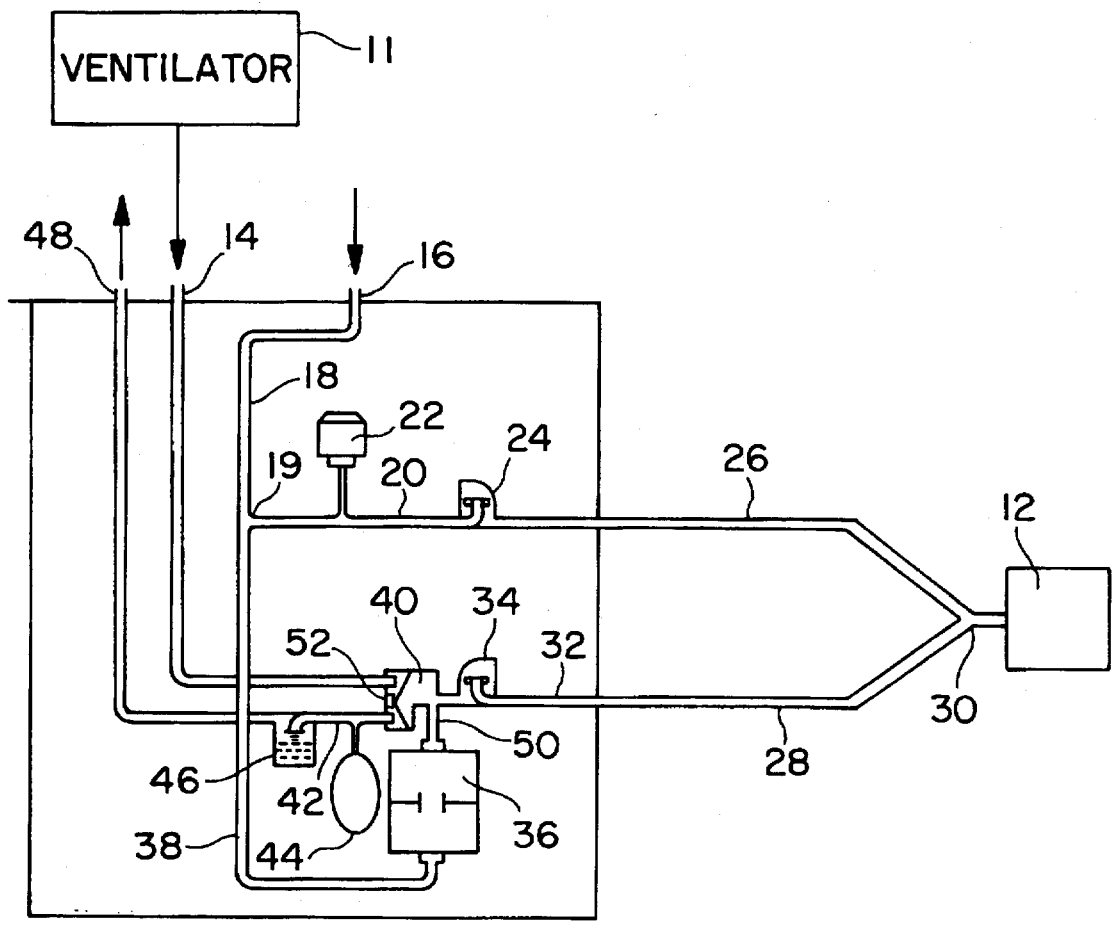
FIG. 1 is a schematic view of an absorber system with which the present invention is applicable.

Referring now to FIG. 1, there is shown a schematic view of an absorber 10 used with an anesthesia system and with which the present invention is applicable. Basically, as is conventional, the absorber 10 is located in the anesthetic system intermediate a ventilator 11 and the patient 12 and is designed to receive gas from the ventilator 11 via ventilator inlet 14. The ventilator 11 provides the breaths to the patient 12 to support breathing of the patient to carry out normal respiration since generally the patient is under anesthesia and unable to breathe fully without support.

A fresh gas inlet 16 receives fresh gas to supplement and make up the gas that may be lost during the process of maintaining the patient 12 under anesthesia and is a constant flow of air into the anesthesia system.

As can be seen, that flow of fresh air from fresh gas inlet 16 enters a circle system through conduit 18 at a tee connection 19 to conduit 20. The fresh gas thus combines with gases circulating through the absorber 10 as will be explained and the conduit 20 may include an oxygen sensor 22 and a check valve 24 to insure that the flow of gas in conduit 20 is always towards the patient 12. Connected to the absorber 10 is a patient circuit comprised of an inhalation limb 26 where the gases are directed toward the patient 12 and an exhalation limb 28 where the exhaled gases are received from the patient 12.

A wye piece 30 connects the inhalation limb 26 and exhalation limb 28 to the patient 12.

Following now the flow of gas from the patient 12, the gases, including exhaled gases containing $CO_2$, enter the absorber 10 and are conveyed via a conduit 32 and another check valve 34, again to prevent reverse flow in the circuit.

The flow of gases thus proceed through a bed of absorbent material 36 where $CO_2$ is removed from the gases. That flow then proceeds via conduit 38 and again joins up with the flow of fresh gas from the conduit 18 at the tee 19 and proceeds generally in a circle back to the patient 12 as explained.

The absorber also contains a bag to ventilator switch 40 that is movable by the operator between two positions. As shown in the solid line position of FIG. 1, the bag to ventilator switch 40 is in the ventilator position where the gas forced from the ventilator passes through the bag to ventilator switch 40 to enter the absorbent material 36 and proceed to breathe the patient 12. Alternately, the user can move the bag to ventilator switch 40 to the bag position shown in the dotted line configuration in FIG. 1, and which shuts off the flow from the ventilator 11 and opens the conduit 42 to the bag 44, allowing the user to breathe the patient by manually squeezing the bag 44.

A pop off valve 46 is also present in the conduit 42 and which relieves the system in the event of excess pressure and which excess gas thus is removed from the overall system via an excess pressure outlet 48.

Accordingly, as can be seen, the bag to ventilator switch 40 has an inlet for receiving gas from the ventilator 11, an inlet for receiving gas from the bag 44 and an outlet 50 that delivers the gas from either of those sources into the circuit for breathing the patient 12. A typical bag to ventilator switch 40 is shown and described in U.S. Pat. No. 4,648,427 of Fruechte et al and assigned to the present applicant and the disclosure of that patent is hereby incorporated herein by reference.

The bag to ventilator switch 40 utilizes a pivoting shaft 52 that is rotated by the user to place the bag to ventilator switch 40 into the desired position where the user can use the bag 44 to ventilate that patient 12 or have the mechanical ventilator 11 carry out the ventilation of the patient 12.

The problem that has been solved by the present invention can now be seen with respect to FIG.1. In applications such as during MRI procedures a ventilator is not used in the ventilation of the patient. In anesthesia machines currently sold for use in MRI applications, the same bag to ventilator switch 40 is a part of the equipment even though there is no need to provide the option of switching the bag to ventilator switch 40 to the ventilator position. As shipped, also, there is normally a protective plastic cap, not shown, that covers the ventilator inlet 14 to protect against introduction of dirt and the like into the absorber 10 and which occludes that ventilator inlet 14.

If that unit is thus used with the protective cap still in place, since there is otherwise no reason to remove the cap, other than in following the advice given by the manufacturer, it is important that the bag to ventilator switch 40 never be moved to the ventilator position. In the event that bag to ventilator switch 40 is moved inadvertently to the ventilator position and the protective cap is still in place covering the ventilator inlet 14, the pop off valve 46 is effectively out of the circuit and the incoming fresh gas from fresh gas inlet 16 can continue to flow into the anesthesia system, including the patient circuit.

As can be seen in FIG. 1, there is no effective outlet for that incoming fresh gas and the internal pressure within the anesthesia system, including within the inhalation limb 26 and exhalation limb 28 can thus increase to a relatively high level. Accordingly, the relatively high pressure can be in communication with the patients lungs and is, of course, undesirable.

Accordingly, with the present invention, a safety absorber switch locking device is provided that prevents the aforementioned situation from taking place, that is, the bag to ventilator switch 40 is immobilized so that it cannot be moved by the user to the ventilator position and, additionally, the locking device further prevents the ventilator inlet 14 from being occluded.

Figure 2:
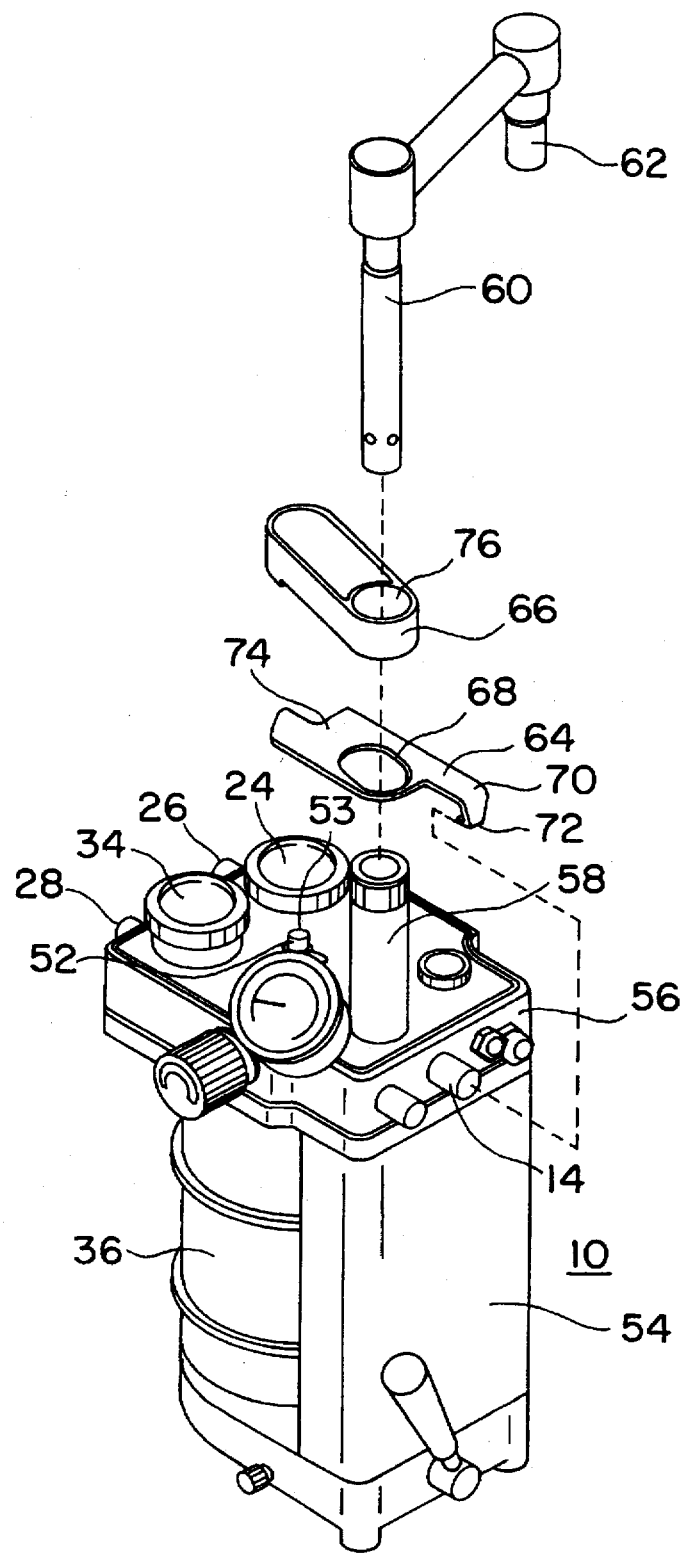
FIG. 2 is an exploded, isometric view of an absorber showing the installation of the subject invention.

Turning now to FIG.2, there is shown an exploded view of absorber 10 and illustrating the assembly of the absorber switch locking device of the present invention. The absorber 10 includes a frame 54 including a head 56 within which is contained many of the components previously discussed. As it may be noted, the unit itself is referred to as an absorber, however the same frame contains the bag to ventilator switch as well other components of the anesthesia system. Those functions are conveniently carried within the absorber 10, however, it is obvious that the bag to ventilator switch could be a separate component in the overall anesthesia system.

Also shown in FIG. 2 is the ventilator inlet 14 and which, as indicated, is normally shipped from the manufacturer with a plastic protective cap in place covering that ventilator inlet 14. Absorber 10 also features, as conventional, an upstanding column 58 formed in the head 56 of frame 54. Extending upwardly from the column 58 is an arm 60 that is shaped so as to have a downwardly extending connection 62. In use, the bag, not shown, is affixed to the connection 62 so that it is within easy reach of the user.

The column 58 is used with the present invention to affix the absorber switch locking device to the absorber 10. As shown the absorber switch locking device comprises a lower component 64 and an upper component 66. Both components 64 and 66 may be formed of a non-magnetic material such as aluminum so as to be sufficiently strong to maintain the integrity of the locking device, yet not be affected by the magnetic field of the MRI apparatus..

In assembly, the lower component 64 has an elongated oval shaped opening 68 that fits over the column 58 and is slid downwardly on column 58 so as to abut the upper surface of head 56. When fitted into position about the column 58, the lower component 64 has an extending arm 70 that has a curled end 72 such that, as assembled in the manner shown in FIG.2, the curled end 72 fits within the open ventilator inlet 14.

Thus, where the lower component 64 is installed by the manufacturer and shipped installed, there is an assurance that no protective cap covers the ventilator inlet 14 and further that no hoses or other conduits can be affixed to the ventilator inlet 14 that could occlude that opening.

A notch 74 is formed in the other end of the lower component 64, the purpose of which will be later explained.

The upper component 66 also has an opening 76 that fits over the column 58, however, in this case, the opening 76 is circular and is configured to fit closely over the outer diameter of the column 58 which is also circular. Again, the upper component 66 therefor fits over and is slid down the column 58 to rest against the head 56 and interfit with the lower component 64. As will be noted, as the upper component 66 is slid into position, it interfits with the upstanding end of the pivoting shaft 52 and locks that pivoting shaft 52 in a fixed position corresponding to the bag to ventilator switch 40 being in the bag position.

In the event the bag to ventilator switch 40 is not in the bag position, the upper component 66 cannot be fastened in position and it is therefore obvious to the installer that the bag to ventilator switch 40 is in the incorrect position.

The upstanding end of the pivoting shaft 52, in normal operation, has a knob for the user to actually switch the bag to ventilator switch 40 between its two positions, however, in assembling the absorber switch locking device of the present invention at the place of manufacture, the knob is not included. In the event the locking device is retrofitted to an absorber in the field, however, the knob must be removed in order to install the absorber switch locking device.

As another standard feature of the pivoting shaft 52, its upper end has a flat portion 53 and which normally mates with the knob, and with this invention, the upper component 66, is readily affixed to the pivoting shaft 52 by means of a set screw (not shown) that is tightened against the flat portion 53 of the pivoting shaft 52.

Figure 3:
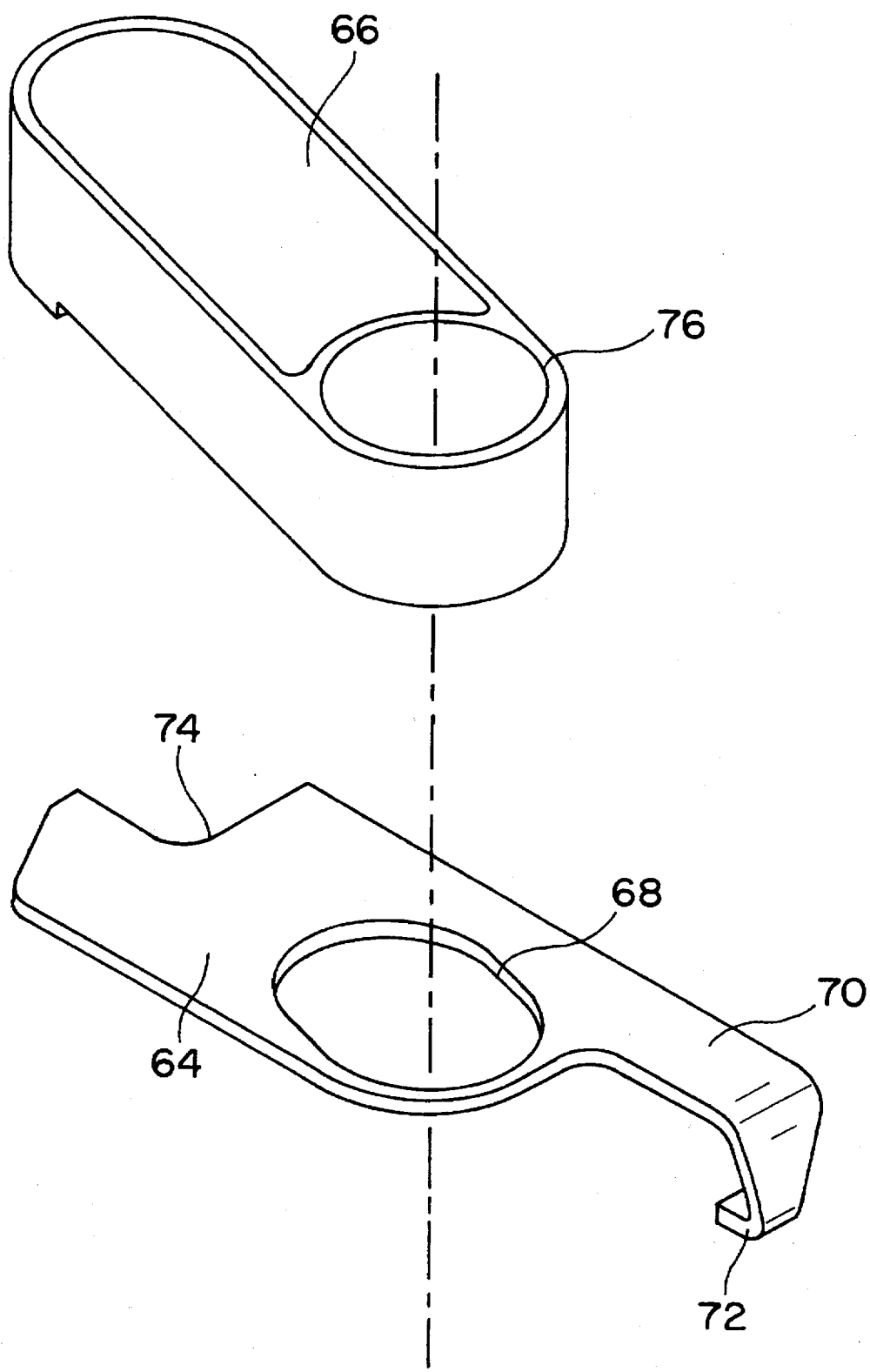
FIG. 3 is an exploded view showing the components of the subject invention.

Turning now to FIG. 3, there is shown an exploded view of the lower component 64 and the upper component 66 positioned so as to be interfitted together. From this view, the curled end 72 of the lower component 64 is more clearly shown as is the oval shaped opening 68, the purpose of which will be later explained. As noted, the opening 76 in the upper component 66 is circular and fits relatively snugly around the column 58 (FIG. 2).

Figure 4:
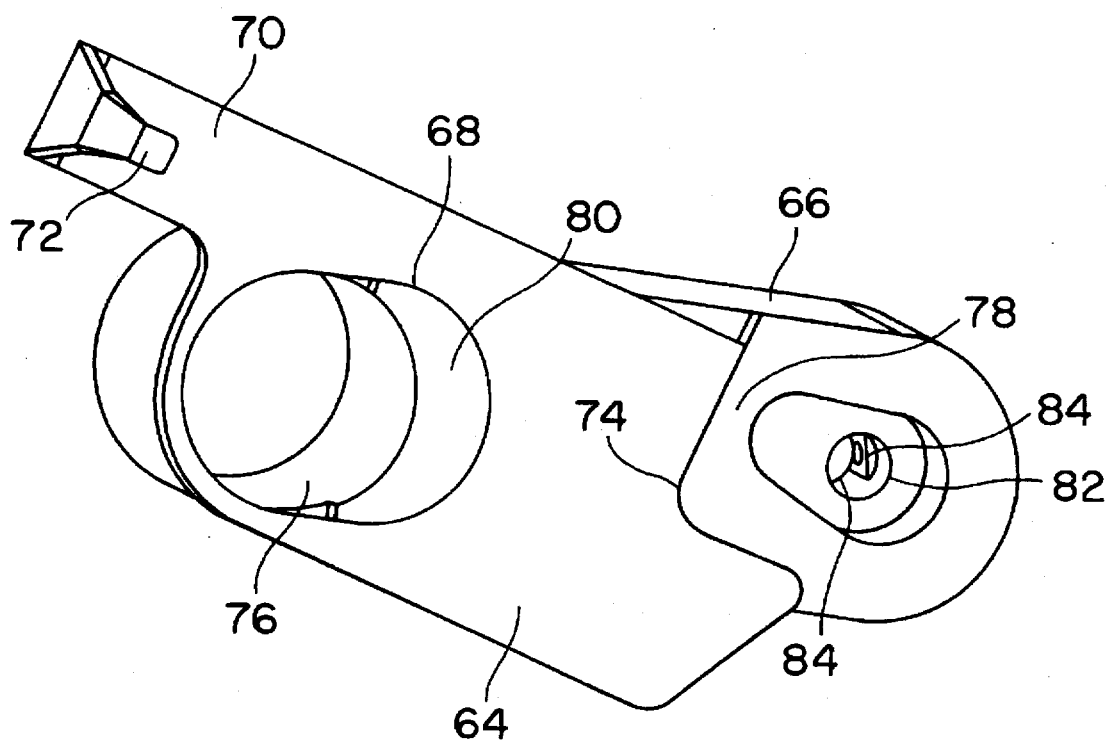
FIG. 4 is an isometric bottom view of the components of the present invention.

Finally, in FIG. 4, there is shown an isometric view of the lower surfaces of the lower component 64 and the upper component 66 interfitted together. As shown the notch 74 of the lower component 64 fits to an raised boss 78 formed in the lower surface of the upper component 66 thereby fitting the two components together.

That interfit is further accomplished by a further raised boss 80 in the upper component 66 that fits within the oval shaped opening 68 while leaving a circular opening in the lower component 64. As such, when the lower component 64 and the upper component 66 are interfitted together, they are constrained from movement with respect to each other by the interfitting of the bosses 78 and 80 into the notch 74 and oval shaped opening 68 of the lower component 64.

As also can be seen in FIG. 4, taken with FIG. 2, a recess 82 is formed in the underside of the upper component 66 and which, when installed as shown in FIG. 2, the recess 82 fits over the upward end of the pivoting shaft 52. That recess 82 has a flat section 84 that abuts the flat portion 53 of the pivoting shaft 52 such that, once installed, the pivoting shaft 52 is rigidly fixed in position and cannot be moved.

As previously explained, the alignment of the flat portion 53 of the pivoting shaft 52 and the flat section 84 of the upper component 66 can only align when the bag to ventilator switch 40 is in the bag position. A hole 86 is also shown within the recess 82 in FIG. 4 for introduction of a set screw to firmly secure the upper component 66 in place on the pivoting shaft 52, thus also securing the locking device to the frame of the absorber.

While the present invention has been set forth in terms of a specific embodiment, it will be understood that the absorber switch locking device herein disclosed may be modified or altered by those skilled in the art to other configurations. Accordingly, the invention is to be broadly construed and limited only by the scope and spirit of the claims appended hereto.

We claim:

1. In an anesthesia system having an absorber, said absorber comprising a housing having a first inlet for receiving gas from a ventilator, and a second inlet for receiving gas from a closed bag, and having an outlet for delivering gas to a patient, switch means within said housing normally movable between a first position where said first inlet is connected to said outlet and a second position where said second inlet is connected to said outlet, the improvement comprising a locking means affixed to said housing and retaining said switch in said second position, said locking means further preventing said first inlet from being closed.

2. In an anesthesia system as defined in claim 1, the improvement wherein said locking means comprises a pair of components interfitted together, one of said components retaining said switch in said second position and the other of said components preventing said first inlet from being closed.

3. In an anesthesia system as defined in claim 2, the improvement wherein said other of said components physically enters said first inlet to prevent said inlet from being closed.

4. In an anesthesia system as defined in claim 2, the improvement wherein one of said pair of components has an opening and the other of said pair of components has a raised boss that fits within said opening to interlock said components together.

5. A bag to ventilator switch for use in an anesthesia system, said switch having a housing having a first inlet adapted to receive gas from a ventilator and a second inlet adapted to receive gas from a flexible bag and having an outlet to provide gas to a patient, said housing enclosing a switch normally movable between a first position wherein said first inlet communicates with said outlet and a second position wherein said second inlet communicates with said outlet, said switch having an upstanding shaft operable to move said switch between said two positions, said upstanding shaft extending exterior of said housing, and locking means affixed to said housing and affixed to said upstanding shaft exterior of said housing to lock said shaft and said switch in said second position and to prevent said upstanding shaft from moving said switch to said first position.

6. A housing as defined in claim 5 wherein said shaft has a flattened portion and said locking means has a recess with a flat portion the interfits with said upstanding shaft to prevent the movement of said switch.

7. A housing as defined in claim 5 wherein said locking means further comprises an elongated arm that physically obstructs said first inlet to prevent the closing of the inlet.

8. A housing as defined in claim 7 where in said elongated arm has a curled portion that physically enters said inlet.

9. A locking device adapted to be affixed to the exterior of an absorber head having an inlet for receiving gas from a ventilator and a switch having an upstanding pivoting shaft to move the switch between two positions, said locking device comprising a first component adapted to be affixed to the head of the absorber and having an extending arm blocking the ventilator inlet to the absorber and a second component adapted to interlock with said first component and having a recess sized to interfit over the upstanding pivoting shaft to lock said upstanding shaft into only one of its two positions.

10. A locking device as defined in claim 9 wherein said recess in said second component has a flat portion to interfit with a flat portion of the upstanding pivoting shaft and further comprises a set screw threaded to said locking means and adapted, when rotated, to press against said flat portion of said shaft to hold said locking means to said shaft.

11. A locking device as defined in claim 10 wherein said extending arm of said first component physically enters said ventilator inlet.

* * * * *